United States Patent
Garrait et al.

(10) Patent No.: US 6,660,880 B2
(45) Date of Patent: Dec. 9, 2003

(54) PROCESS FOR THE PREPARATION OF HYDROXY 4-METHYL THIOBUTYRIC ACID ESTERS

(75) Inventors: Michel Garrait, Millery (FR); Claude Casse, Decines (FR); George Gros, Antony (FR)

(73) Assignee: Adisseo Ireland Limited, Dublin (IE)

( * ) Notice: Subject to any disclaimer, the term of this patent is extended or adjusted under 35 U.S.C. 154(b) by 0 days.

(21) Appl. No.: 09/778,191

(22) Filed: Feb. 7, 2001

(65) Prior Publication Data

US 2001/0029308 A1 Oct. 11, 2001

(30) Foreign Application Priority Data

Feb. 7, 2000 (WO) .............................. PCT/EP00/01324

(51) Int. Cl.$^7$ ..................... C07C 319/20; C07C 323/52; C07C 327/00; C07C 69/52
(52) U.S. Cl. ................... 560/195; 562/26; 562/581; 564/129; 426/2
(58) Field of Search .................. 562/581, 26; 560/195, 560/152; 426/2; 564/129

(56) References Cited

U.S. PATENT DOCUMENTS

| 2,745,745 A | * | 5/1956 | Blake et al. ................. 514/557 |
| 3,761,518 A | * | 9/1973 | Haglid ........................ 562/581 |
| 4,310,690 A | * | 1/1982 | Cummins .................... 562/581 |
| 4,353,924 A | * | 10/1982 | Baker et al. ................. 514/557 |
| 4,579,962 A | * | 4/1986 | Takano ........................ 556/131 |
| 5,386,056 A | * | 1/1995 | Matsuoka .................... 562/526 |

FOREIGN PATENT DOCUMENTS

| CA | 694592 | * | 9/1964 |

\* cited by examiner

Primary Examiner—Alan L. Rotman
Assistant Examiner—Taylor V Oh
(74) Attorney, Agent, or Firm—Connolly Bove Lodge and Hutz LLP

(57) ABSTRACT

A process, for the preparation of an ester of 2-hydroxy-4-methylthiobutyric acid which is substantially in the monomeric form, which process, being capable of industrial application and which comprises reacting 2-hydroxy-4-methylthiobutyric acid with an alcohol in the presence of water and an acid catalyst at a temperature of from 30 to 150° C. wherein the acid is the direct product of the hydrolysis of 2-hydroxy-4-methylthiobutyronitrile.

31 Claims, No Drawings

PROCESS FOR THE PREPARATION OF HYDROXY 4-METHYL THIOBUTYRIC ACID ESTERS

The present invention relates to an industrial process for the preparation of 2-hydroxy-4-methylthiobutyric acid esters.

2-Hydroxy-4-methylthiobutyric acid is known to be used as a methionine analogue for feeding breeding animals. This product is marketed under the trade names Rhodimet AT 88™ and Alimet™.

It is known to prepare the 2-hydroxy-4-methylthiobutyric acid by various processes by hydrolysing the 2-hydroxy-4-methylthiobutyronitrile. The hydrolysis can be carried out with an inorganic acid such as hydrochloric or sulphuric acid. Alternatively this reaction can be carried out by enzymatic hydrolysis.

The ester of 2-Hydroxy-4-methylthiobutyric acid is also used as a means of introducing methionine to animals and indeed may be used as an alternative to the acid. It has been found that the ester form is more stable than the acid and that methionine is released from the ester at a rate faster than from the acid form. Thus, the ester form ha become a more favoured means of introducing methionine into the bloodstream of the animal, in particular to ruminants as disclosed in French Patent Application No. 98 14249.

The ester of 2-Hydroxy-4-methylthiobutyric acid may be prepared by esterification of the hydrochloride salt of the acid and then reacting this salt with the alcohol. Such processes are known from U.S. Pat. Nos. 3,850,987 and 3,761,518. It is also possible to prepare the 2-hydroxy-4-methylthiobutyric acid esters by a process which comprises hydrating 2-hydroxy-4-methylthiobutyronitrile with sulphuric acid and then esterifying the product obtained. Such processes are disclosed in U.S. Pat. Nos. 4,524,077 and 4,912,257 and WO 96/40630.

It is known in the art that the monomeric form of 2-Hydroxy-4-methylthiobutyric acid or derivatives thereof exhibit greater biological efficacy than the dimeric and oligomeric forms. Thus, if the product is to be used as an additive in animal feed, it is preferred to produce a product which contains as little as possible dimers and oligomers.

Therefore, when starting from the acid or the salt thereof, in the production of the ester, it is essential that the acid or salt is essentially in the monomeric form. To reduce the amount of dimers and oligomers in the acid, the acid may be purified by various means such as liquid/liquid extraction. This treated acid may then be used to produce the ester.

We have found that 2-hydroxy-4-methylthiobutyric acid esters containing a small amount of oligomers can be produced by the esterification of 2-hydroxy-4-methylthiobutyric acid without the need to pre-treat the acid before the esterification reaction when the esterification reaction is carried out under specific conditions. Indeed, we have found that the ester may be produced from the acid which contains a high amount of oligomers and yet using the process of the present invention, the resulting ester is low in oligomers. Furthermore, we have found that this process is particularly suitable for use as an industrial process.

Accordingly, the present invention provides a process, for the preparation of an ester of 2-hydroxy-4-methylthiobutyric acid which is substantially in the monomeric form, which process, being capable of industrial application and which comprises reacting 2-hydroxy-4-methylthiobutyric acid with an alcohol in the presence of water and an acid catalyst at a temperature of from 30 to 150° C. wherein the acid is the direct product of the hydrolysis of 2-hydroxy-4-methylthiobutyronitrile.

It will of course be understood by the person skilled in the art that the 2-hydroxy-4-methylthiobutyric acid obtained as a direct product of the hydrolysis of 2-hydroxy-4-methylthiobutyronitrile from an industrial process comprises a mixture of monomers, dimers and higher oligomers.

The process of the present invention provides the advantage over the prior art in that there is no need to purify of the acid prior to esterification. This is, of course, an important advantage in an industrial process, avoiding the use of additional large equipment.

In the process of the present invention 2-hydroxy-4-methylthiobutyric acid obtained directly from the hydrolysis of 2-hydroxy-4-methylthiobutyronitrile is reacted with an alcohol. The acid is, thus, likely to be a direct product of an industrial process and will therefore be a mixture of monomers, dimers and other oligomers. The acid may also comprise impurities such as water, sulphuric acid and ammonium sulphate. In particular, the acid may be produced from an industrial process for the production of 2-hydroxy-4-methylthiobutyric acid and may be, for example, Rhodimet™ AT 88, sold by Rhône Poulenc. Using the process of the present invention, this untreated acid, may be used directly to produce the ester and it is surprising that the resulting ester is low in oligomer content.

The alcohol, suitable for use in the present process, may be an aliphatic alcohol containing 1 to 10 carbon atoms. The alcohol may be linear or branched. Preferably, the alcohol is branched, especially isopropyl alcohol. The use of isopropyl alcohol is particularly preferred as the 2-hydroxy-4-methylthiobutyric acid isopropyl ester has a high biological efficacy.

The acid and the alcohol is suitably reacted in a molar ratio of from 1 to 20. Where the process is operated as a continuous process, the overall molar ratio of acid to alcohol is preferably 1 to 10. The amount of alcohol in the continuous reaction may be maintained at the desired level by recycle. Where the process is operated as a batch process, the molar ratio of acid to alcohol is preferably from 2 to 10. Any unreacted alcohol may be recycled.

The process of the present invention is carried out in the presence of water. The water may be added to the reaction vessel or the water may be produced in-situ. In particular, it has been found that the conversion of acid oligomers is particularly favoured when water is present at the beginning of the esterification reaction.

The process is carried out in the presence of an acid catalyst. Catalysts suitable for use in the process include acids having a $pK_a$ of less than 3, for example sulphuric acid, xylene sulphonic acid and trifluoroacetic acid. Alternatively, an acid resin may be used to catalyse the process, especially a sulphonic acid resin, for example Amberlyst 15 as produced by Rohm & Haas. The process may also be catalysed using alumina or an aluminosilicate, for example a zeolite or through the use of an enzyme, for example, esterase.

The catalyst may be present in the reaction process in a concentration of suitably at least 0.01 mole of catalyst per mole of 2-hydroxy-4-methylthiobutyric acid, preferably from 0.02 to 0.2 mole of catalyst per mole of acid.

The process may be carried out under atmospheric or elevated pressure. Where the process is carried out under elevated pressure, the pressure may be any suitable pressure, for example up to 50 bar.

The process is carried at a temperature of from 30 to 150° C. Preferably, the process is carried out at a temperature of from 60 to 120° C., especially from 80 to 100° C.

The process may be carried out continuously, semi-continuously or batchwise. In particular for an industrial process, it is preferred to operate a continuous process.

As the process involves an equilibrium reaction, it is preferred to continuously remove water formed in the reaction in order to shift the reaction towards the ester products. The water formed in the reaction may be removed by any suitable means appropriate to an industrial process, for example by distillation. In some cases, the alcohol may be added to form an azeotrope and separated by azeotropic distillation.

The resulting product stream comprises the ester, water, unreacted alcohol, unreacted acid, a small amount of acid oligomers and catalyst. The ester product may be separated from the remaining components of the product stream by any suitable treatment method.

Where the catalyst used in the process is an acid catalyst, the unreacted catalyst in the product stream may be removed by the addition of a base, namely neutralisation. This neutralisation step may be carried out at any stage. Where the catalyst is sulphuric acid, this step may be carried out by the addition of a base having a $pK_a$ greater than 8, for example ammonia or ammonium hydroxide or sodium hydroxide. Where the catalyst used in the process is a solid, such as a resin, it is preferred at the end of the reaction to remove the catalyst from the product stream by filtration. Additional solid by-products may also be separated and removed from the product stream by filtration.

The remaining by-products may be separated from the ester by distillation and/or evaporation.

One suitable method for separation of the ester from the by-products may involve an initial distillation step to remove the light products, namely the unreacted alcohol and water. The resulting stream, optionally, may then be treated to neutralise the acid catalyst acid as described above, followed by a third step of distillation to remove the heavy products. The distillation products may be recycled back to the reactor.

Alternatively, the ester product may be isolated by alcohol evaporation, followed by short term distillation, for example using thin film evaporator.

The treated product stream, comprising the ester may then be washed. The washing step is suitably carried out by the addition of water, optionally comprising an additive to enhance the decantation. Suitable additives include salts such as ammonium sulphate. The resulting mixture will separate into an organic phase and an aqueous phase. The organic phase may then be isolated and, if desired, washed at least one more time. The resulting organic phase may be distilled to separate the ester from any remaining, unwanted by-products. The unwanted by-products separated from the ester product may be recycled back to the reactor.

The resulting product stream comprises a high yield of monomeric ester, at least 55%, more typically at least 90%, especially at least 95%.

The present invention will now be illustrated with reference to the following examples:

EXAMPLE 1

Synthesis of 2-hydroxy-4-methylthiobutyric acid isopropyl Ester (MHBI) Using an Acid Catalyst Step (a)—Esterification: 170.7 g of Rhodimet AT88, containing 88% acid (68% monomers and 20% oligomers) and 12% water, and 180.3 g of isopropanol were loaded into a reactor. 19.6 g of 95% sulphuric acid was added whilst maintaining the temperature at reflux temperature. The acid was added in one aliquot. After the acid had been introduced into the reactor, the reaction was maintained at reflux temperature for two hours. The temperature was increased to 90° C. Additional isopropanol (420 g) was added continuously over 5 hours and the azeotrope of alcohol and water was removed continuously.

Step (b)—Neutralisation/Removal of Water: The reaction mixture was cooled to 40° C. and then neutralised to pH 7/8 by the addition of 22 g of 32% weight ammonium hydroxide. The resulting product was distilled at 60° C. under a pressure of 50 millibar for approximately 1 hour.

Step (c)—Washing: The distillate product was then washed by adding 95 g of 5% aqueous ammonium sulphate, with stirring. The resulting mixture was stirred at a temperature of 40° C. for 15 minutes. The stirring was stopped and the mixture left to stand at 40° C. for 30 minutes. The aqueous phase was then separated from the organic phase. The organic phase was washed again with 30 g of water.

Step (d)—Removal of Water/Isopropanol: The organic phase was then distilled at 100° C. under a pressure of 5 mbar for approximately 2 hours to yield a product stream comprising mainly the ester. The resulting product stream was analysed and was found to contain 92% monomeric ester, 5% dimer and 2.5% unreacted acid.

EXAMPLE 2

Synthesis of 2-hydroxy-4-methylthiobutyric acid isopropyl ester (MHBI) Using a Resin Catalyst 179.6 g of Rhodimet AT88, containing 88% acid (68% monomers and 20% oligomers) and 12% water, and 179.6 g of isopropanol were loaded into a reactor. 30 g of Amberlyst 15 resin was introduced into the reactor whilst maintaining the temperature at reflux temperature. The reaction was maintained at this temperature for 5 hours. Analysis of the resulting product showed a 65% conversion of acid (monomers and oligomers) with a yield of 60% monomeric ester and 5% dimeric ester. This example shows the feasibility of using a resin catalyst.

EXAMPLE 3

Esterification of the By-Product Stream 101 g of a distillation stream containing 40 g dimeric ester, 16 g monomeric acid and 6.5 g dimeric acid; 224 g of isopropanol and 17 g of water were loaded into a reactor. 11.5 g of 95% sulphuric acid was added in one aliquot. After the acid had been introduced the reaction was maintained at reflux temperature for five hours. The reaction was terminated and product stream analysed. It was found to contain 55 g monomer ester, 17 g monomer acid, 4 g dimer ester and 3 g dimer acid.

This example proves the feasibility of recycling a stream containing a substantial quantity of the ester dimers.

EXAMPLE 4

Synthesis of 2-hydroxy-4-methylthiobutyric acid isopropyl ester (HMBI) Using an Acid Catalyst with Recycling of the Heavy Products and Purification by Distillation Step (a)—Recycling of Heavy Products: 113 g of a recycle stream containing 41 g of monomeric ester, 19 g of monomeric acid, 11 g of dimeric ester and 88 g isopropanol were loaded into a reactor. 10 g of 95% sulphuric acid was added in one aliquot. The reaction was then maintained at reflux temperature for one hour. The resulting mixture contained 61 g of monomeric ester, 11 g of monomeric acid, 7.9 g of dimeric ester and 2.1 g of dimeric acid.

Step (b)—Esterification: 170 g of Rhodimet AT88, containing 68% monomers and 20% oligomers) and 12% water, and 168 g of isopropanol were loaded into a reactor whilst maintaining the temperature at reflux temperature. The reaction was maintained at reflux temperature for one hour. The temperature was increased to 90° C. and additional isopropanol (300 g) then added continuously over 1.5 hours. The azeotrope of alcohol and water was removed continuously.

Step (c)—Neutralisation/Removal of Water and Isopropanol: The mixture was then neutralised to pH 2.5/3.5 by the addition of 16.5 g of 50% weight sodium hydroxide. The resulting product was distilled at 80° C. under a pressure of 50 millibar for approximately 1 hour.

Step (d)—Distillation: The distillate product was then distilled at about 150° C. under a pressure of 10 milibar for approximately 1 hour. 183 g of distilled product was obtained. Analysis of the product indicated the presence of 97% monomeric ester.

Step (e)—Washing of Distillate: The remaining distillate (119 g) was washed with 39 g of water at a temperature of about 70° C. The aqueous phase was separated from the organic phase. 10% of the organic phase was purged to yield 113 g of product containing 41 g of monomeric ester, 19 g of monomeric acid, 11 g of dimeric ester and 7.6 g of dimeric acid.

EXAMPLE 5

Synthesis of 2-hydroxy-4-methylthiobutyric acid isopropyl ester (HMBI) Using an Acid Catalyst The procedure of Example 4 was repeated but omitting the neutrilisation step (c). Steps (a) and (b) were as in Example 4.

Step (c): Distillation

The product was distilled at about 150° C. under a pressure of 10 millibar for approximately 1 hour. The distillation proceeded at a rate slower than that of Example 4. 4.83 g of distilled product was obtained. 187 g of distillate remained in the boiler.

Analysis of the two product streams indicated the presence of 93% monomeric ester and approximately 3% impurity. The distillate stream comprised 8.3% monomeric ester and 24% dimeric ester.

EXAMPLE 6

Synthesis of 2-hydroxy-4-methylthiobutyric acid isopropyl ester (HMBI) Using Continuous Reactive Distillation The distillation column used was an adiabatic Older-Shaw column with internal diameter of 55 mm and containing 40 plates, provided with a reboiler of capacity of 2 liters. A flow of 683 g/hour containing 91% weight of AT88 and 9% weight of 95% sulphuric acid was preheated to approximately 90° C. and fed to the head of the column. A flow of 3190 g/hour of isopropanol, preheated to approximately 80° C., was introduced into the reboiler. Once the steady state conditions were reached (reboiler temperature of 88° C. and head of column temperature of 91° C.) condensates were withdrawn at a rate of 1895 g/hour from the head of the column and distillates were withdrawn at a rate of 1978 g/hour from the bottom of the column.

Analysis of the distillate indicated 22% monomeric ester, 4.7% dimeric ester, 1% monomeric acid and 3% dimeric acid.

EXAMPLE 7

Purification of HMBI by Continuous Distillation

The product mixture of Example 6 was purified in two stages with a film evaporator of 2 cm diameter and height of 20 cm and heating in an oil bath.

(a) Removal of water and oil—A product stream as obtained in example 6 was fed, at a rate of 200 g/hour onto the film evaporator at 30° C. and under a pressure of 10 millibar. A condensate stream was continuously withdrawn, at a rate of 88 g/hour, from the head of the column. A distillate stream was continuously withdrawn, at a rate of 112 g/hour, from the bottom of the column.

(b) Purification—The distillate obtained in step (a) was fed onto a film evaporator at a flow rate of 810 g/hour, at a temperature of 182° C. and under a pressure of 6 millibar. A condensate stream was continuously withdrawn, at a rate of 394 g/hour, from the head of the column. A distillate stream was continuously withdrawn, at a rate of 288 g/hour, from the bottom of the column.

Analysis of the product failed to identify the impurities as found in the product stream of Example 5. The condensate contained 92% monomeric ester, 1.5% dimeric ester and 0.6% acid. The distillate contained 3.2% monomeric ester, 5.6% dimeric ester, 0.9% monomeric acid and 1% dimeric acid.

What is claimed is:

1. A process for the preparation of an ester of 2-hydroxy-4-methylthiobutyric acid which is substantially in the monomeric form, which process comprises reacting 2-hydroxy-4-methylthiobutyric acid with an alcohol in the presence of water and an acid catalyst in a reactor at a temperature of from 30 to 150° C. wherein the acid is the direct product of the hydrolysis of 2-hydroxy-4-methylthiobutyronitrile, wherein said alcohol is selected from the group consisting of aliphatic alcohols containing 1 to 10 carbon atoms and wherein said acid catalyst is selected from the group consisting of acids having a pKa of less than 3, and acid resins.

2. A process as claimed in claim 1, in which the temperature is from 60 to 120° C.

3. A process as claimed in claim 2, in which the temperature is from 80 to 100° C.

4. A process as claimed in claim 1, in which the alcohol is linear or branched.

5. A process as claimed in claim 4, in which the alcohol is a branched alcohol.

6. A process as claimed in claim 5, in which the alcohol is isopropanol.

7. A process as claimed in claim 1, in which the molar ratio of 2-hydroxy-4-methylthiobutyric acid to alcohol is from 1 to 10.

8. A process as claimed in claim 1, in which the acid catalyst is selected from the group consisting of sulphuric acid, xylene sulphonic acid and trifluoroacetic acid.

9. A process as claimed in claim 8, in which the acid catalyst is sulphuric acid.

10. A process as claimed in claim 1, in which the acid catalyst is a sulphonic acid resin.

11. A process as claimed in claim 1, in which water is continuously withdrawn from the reaction.

12. A process as claimed in claim 1, in which by-products are formed and the by-products are separated from the ester product by a treatment process with distillation.

13. A process as claimed in claim 12, in which the distilled by-products are recycled to the reactor.

14. A process as claimed in claim 1, wherein said process is a continuous process.

15. A process as claimed in claim 1, wherein said process is a batch process.

16. A process for the preparation of an ester of 2-hydroxy-4-methylthiobutyric acid which is substantially in the monomeric form, which process comprises reacting 2-hydroxy-4-methylthiobutyric acid with an alcohol in the presence of water and a catalyst in a reactor at a temperature of from 30 to 150° C. wherein the acid is the direct product of the hydrolysis of 2-hydroxy-4-methylthiobutyronitrile, wherein said alcohol is selected from the group consisting of aliphatic alcohols containing 1 to 10 carbon atoms and wherein said catalyst is selected from the group consisting of alumina and aluminosilicates.

17. A process for the preparation of an ester of 2-hydroxy-4-methylthiobutyric acid which is substantially in the monomeric form, which process comprises reacting 2-hydroxy-4-methylthiobutyric acid with an alcohol in the presence of water and a catalyst in a reactor at a temperature of from 30 to 150° C. wherein the acid is the direct product of the hydrolysis of 2-hydroxy-4-methylthiobutyronitrile, wherein said alcohol is selected from the group consisting of aliphatic alcohols containing 1 to 10 carbon atoms and wherein said catalyst comprises an esterase enzyme.

18. A process as claimed in claim 16, in which the alcohol is linear or branched.

19. A process as claimed in claim 17, in which the alcohol is linear or branched.

20. A process as claimed in claim 16, in which water is continuously withdrawn from the reaction.

21. A process as claimed in claim 17, in which water is continuously withdrawn from the reaction.

22. A process as claimed in claim 16, in which the temperature is from 60 to 120° C.

23. A process as claimed in claim 17, in which the temperature is from 60 to 120° C.

24. A process as claimed in claim 16, in which the alcohol is isopropanol.

25. A process as claimed in claim 17, in which the alcohol is isopropanol.

26. A process as claimed in claim 16, in which the molar ratio of 2-hydroxy-4-methylthiobutyric acid to alcohol is from 1 to 10.

27. A process as claimed in claim 17, in which the molar ratio of 2-hydroxy-4-methylthiobutyric acid to alcohol is from 1 to 10.

28. A process as claimed in claim 16, in which by-products are formed and the by-products are separated from the ester product by a treatment process with distillation.

29. A process as claimed in claim 17, in which by-products are formed and the by-products are separated from the ester product by a treatment process with distillation.

30. A process as claimed in claim 16, in which the distilled by-products products are recycled to the reactor.

31. A process as claimed in claim which the distilled by-products products are recycled to the reactor.

* * * * *

UNITED STATES PATENT AND TRADEMARK OFFICE
CERTIFICATE OF CORRECTION

PATENT NO.     : 6,660,880 B2
DATED          : December 9, 2003
INVENTOR(S)    : Michel Garrait et al.

It is certified that error appears in the above-identified patent and that said Letters Patent is hereby corrected as shown below:

<u>Column 8,</u>
Line 26, "claim which" should read -- claim 17, in which --.

Signed and Sealed this

Twenty-second Day of June, 2004

JON W. DUDAS
*Acting Director of the United States Patent and Trademark Office*